United States Patent
Yan et al.

(10) Patent No.: US 10,987,373 B2
(45) Date of Patent: Apr. 27, 2021

(54) DNA ORIGAMI NANOSTRUCTURES FOR TREATMENT OF ACUTE KIDNEY INJURY

(71) Applicants: Hao Yan, Chandler, AZ (US); Dawei Jiang, Madison, WI (US); Zhilei Ge, Tempe, AZ (US); Hyung-jun Im, Seoul (KR); Christopher England, Madison, WI (US); Peng Huang, Guangdong (CN); Chunhai Fan, Shanghai (CN); Weibo Cai, Madison, WI (US)

(72) Inventors: Hao Yan, Chandler, AZ (US); Dawei Jiang, Madison, WI (US); Zhilei Ge, Tempe, AZ (US); Hyung-jun Im, Seoul (KR); Christopher England, Madison, WI (US); Peng Huang, Guangdong (CN); Chunhai Fan, Shanghai (CN); Weibo Cai, Madison, WI (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 38 days.

(21) Appl. No.: 16/492,099

(22) PCT Filed: Mar. 8, 2018

(86) PCT No.: PCT/US2018/021599
§ 371 (c)(1),
(2) Date: Sep. 6, 2019

(87) PCT Pub. No.: WO2018/165465
PCT Pub. Date: Sep. 13, 2018

(65) Prior Publication Data
US 2020/0101101 A1    Apr. 2, 2020

Related U.S. Application Data

(60) Provisional application No. 62/469,064, filed on Mar. 9, 2017.

(51) Int. Cl.
| | |
|---|---|
| *A61K 31/711* | (2006.01) |
| *A61P 13/12* | (2006.01) |
| *A61K 9/51* | (2006.01) |
| *A61K 49/00* | (2006.01) |
| *G01N 33/543* | (2006.01) |
| *G01N 33/58* | (2006.01) |
| *A61K 9/00* | (2006.01) |
| *B82Y 5/00* | (2011.01) |

(52) U.S. Cl.
CPC .............. *A61K 31/711* (2013.01); *A61K 9/51* (2013.01); *A61K 49/0093* (2013.01); *A61P 13/12* (2018.01); *G01N 33/54346* (2013.01); *G01N 33/587* (2013.01); *A61K 9/0019* (2013.01); *B82Y 5/00* (2013.01); *C12N 2795/14121* (2013.01); *C12N 2795/14142* (2013.01); *G01N 2800/347* (2013.01)

(58) Field of Classification Search
CPC .... A61K 31/711; A61K 31/7088; A61K 9/51; A61K 49/0093; A61K 9/0019; A61P 13/12; G01N 33/54346; G01N 33/587; G01N 2800/347; B82Y 5/00; C12N 2795/14121; C12N 2795/14142; C12N 2795/14141
See application file for complete search history.

(56) References Cited

U.S. PATENT DOCUMENTS

| | | | |
|---|---|---|---|
| 8,501,923 | B2 | 8/2013 | Rothemund |
| 8,552,167 | B2 | 10/2013 | Chang et al. |
| 8,685,894 | B2 | 4/2014 | Chaput et al. |
| 8,895,072 | B2 | 11/2014 | Yan et al. |
| 9,944,923 | B2 | 4/2018 | Blattman et al. |
| 10,189,874 | B2 | 1/2019 | Han et al. |
| 10,669,534 | B2 | 6/2020 | Fu et al. |
| 2009/0018028 | A1 | 1/2009 | Lindsay et al. |
| 2010/0009868 | A1 | 1/2010 | Yan et al. |
| 2014/0031416 | A1 | 1/2014 | Chang et al. |
| 2015/0004193 | A1 | 1/2015 | Chang et al. |
| 2015/0017201 | A1 | 1/2015 | Chang et al. |
| 2016/0145679 | A1 | 5/2016 | Yan et al. |
| 2017/0051338 | A1 | 2/2017 | Manetto |
| 2017/0269095 | A1 | 9/2017 | Lee |
| 2018/0044663 | A1 | 2/2018 | Yan |
| 2018/0216102 | A1 | 8/2018 | Blattman et al. |

(Continued)

FOREIGN PATENT DOCUMENTS

| | | |
|---|---|---|
| WO | 2006124089 A1 | 11/2006 |
| WO | 2007139849 A2 | 12/2007 |

(Continued)

OTHER PUBLICATIONS

Bosch, et al., 'Rhabdomyolysis and Acute Kidney Injury', The New England Journal of Medicine, 361; 1, Jul. 2, 2009, pp. 62-72.

(Continued)

*Primary Examiner* — Robert S Cabral
(74) *Attorney, Agent, or Firm* — Schwabe, Williamson & Wyatt, P.C.

(57) ABSTRACT

Disclosed herein are methods of treating acute kidney injury. The A method can include administering a sufficient amount of a DNA origami nanostructure to a subject afflicted with AKI to increase an excretory function of said subject. In some examples, the DNA origami nanostructure includes a scaffold strand and a plurality of staple strands, in which the scaffold strand comprises a M1 3 viral genome having a length of 7249 base pairs; and each staple strand of the plurality of staple strands has a length of about 20 to 60 base pairs.

8 Claims, 12 Drawing Sheets

(56) References Cited

U.S. PATENT DOCUMENTS

| | | |
|---|---|---|
| 2019/0144491 A1 | 5/2019 | Han et al. |
| 2019/0240248 A1 | 8/2019 | Yan et al. |

FOREIGN PATENT DOCUMENTS

| | | |
|---|---|---|
| WO | 2008033804 A2 | 3/2008 |
| WO | 2008033848 A2 | 3/2008 |
| WO | 2010060030 A1 | 5/2010 |
| WO | 2011049750 A1 | 4/2011 |
| WO | 2013119676 A1 | 8/2013 |
| WO | 2014134338 A1 | 9/2014 |
| WO | 2014200933 A1 | 12/2014 |
| WO | 2015130805 A1 | 9/2015 |
| WO | 2019109707 A1 | 6/2019 |
| WO | 2019140140 A1 | 7/2019 |
| WO | 2019147308 A2 | 8/2019 |
| WO | 2019147308 A9 | 8/2019 |
| WO | 2019147309 A2 | 8/2019 |
| WO | 2019147309 A9 | 8/2019 |
| WO | 2019152957 A1 | 8/2019 |
| WO | 2020036654 A2 | 2/2020 |

OTHER PUBLICATIONS

Jiang, et al., 'Multiple-Armed Tetrahedral DNA Nanostructures for Tumor-Targeting, Dual-Modality in Vivo Imaging', ACS Applied Materials & Interfaces, 2016, vol. 8, No. 7, pp. 4378-4384.

Lameire, et al., 'The prevention of acute kidney injury an in-depth narrative review', NDT Plus (2009) 2:1-10.

Okholm, et al., 'The utility of DNA nanostructures for drug delivery in vivo', Expert Opinion on Drug Delivery, 2017, vol. 14, No. 2, pp. 137-139.

Pei, et al., 'Functional DNA Nanostructures for Theranostic Applications', Accounts of Chemical Research, 2013, vol. 47, No. 2, pp. 550-559.

Rahman, et aL, 'Acute Kidney Injury: A Guide to Diagnosis and Management', American Family Physician, vol. 86, No. 7, Oct. 1, 2012, pp. 631-639.

Rewa, et al., Acute kidney injury—epidemiology, outcomes and economics, Nat. Rev. Nephrol. 10, Jan. 21, 2014, pp. 193-207.

The International Bureau of WIPO, International Preliminary Report on Patentability in PCT/US2018/021599, dated Sep. 19, 2019, 8 pages.

U.S. Appl. No. 16/642,792, Chang et al., filed Feb. 27, 2020.

U.S. Appl. No. 16/812,225, Fu et al., filed Mar. 6, 2020.

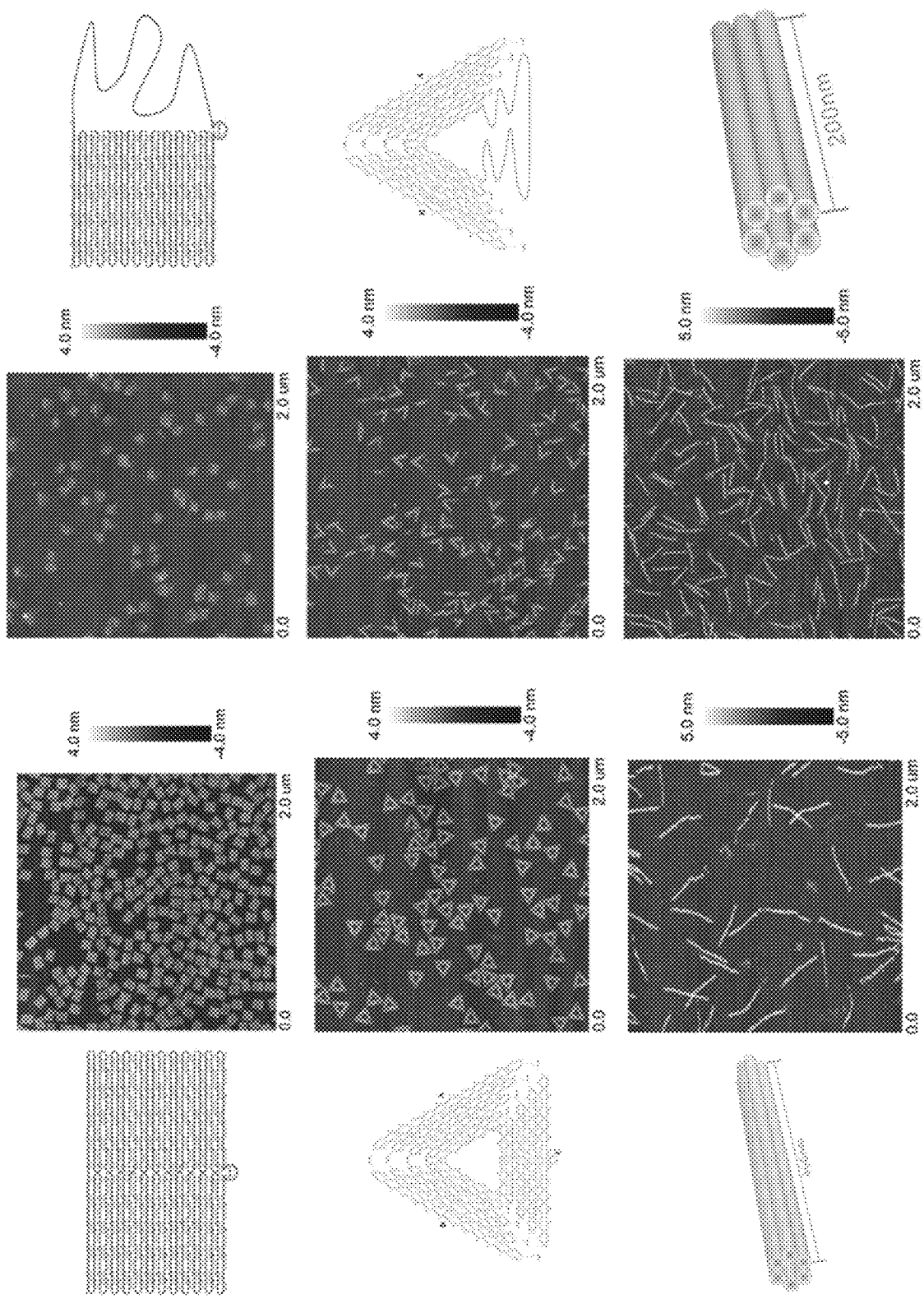

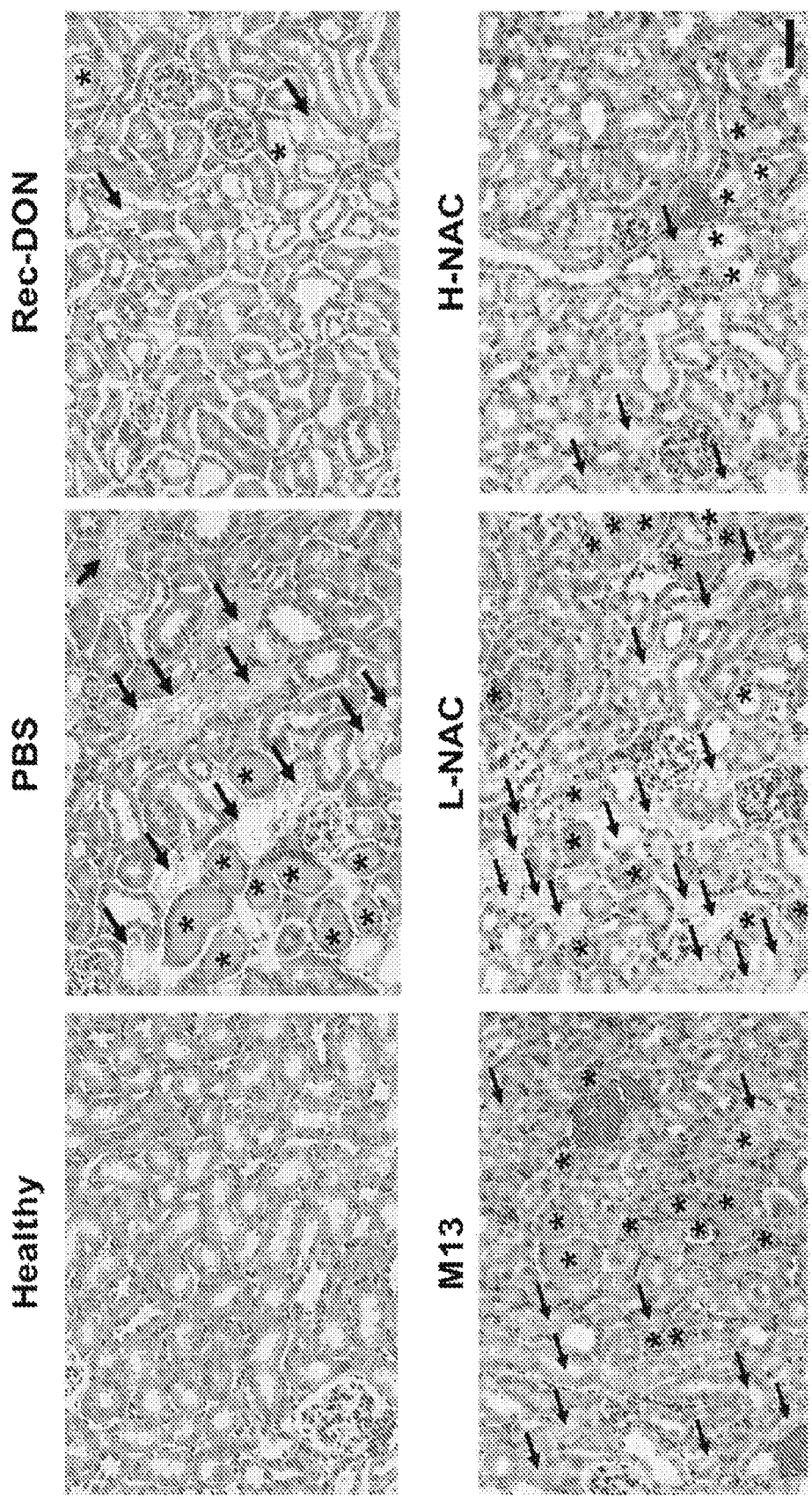

DNA ORIGAMI NANOSTRUCTURES FOR TREATMENT OF ACUTE KIDNEY INJURY

CROSS REFERENCE TO RELATED APPLICATION

This application is a U. S. National stage Application under 35 USC 371 of International Application PCT/US2018/021599, filed Mar. 8, 2018, which claims the benefit of U.S. Provisional Patent Application No. 62/469,064, filed Mar. 9, 2017, which is incorporated herein by reference in its entirety.

TECHNICAL FIELD

The present technology disclosed herein relates to DNA nanotechnology and, more particularly, to DNA origami nanostructures and their in vivo applications.

BACKGROUND

DNA nanotechnology has been developed for over three decades, and most researchers envisioned the broad potential of DNA origami nanostructures (DONs) for in vivo application due to their biocompatibility and biodegradability. However, the biological behavior of DONs in vivo has not been fully understood, let alone exploiting DONs for preclinical or clinical uses.

Acute kidney injury (AKI), also called acute renal failure (ARF), is a rapid loss of kidney function. Its causes are numerous and include low blood volume from any cause, exposure to substances harmful to the kidney, and obstruction of the urinary tract. AKI is diagnosed on the basis of characteristic laboratory finding, such as elevated blood creatinine, or inability of the kidneys to produce sufficient amounts of urine.

Acute kidney injury is diagnosed on the basis of clinical history and laboratory data. A diagnosis is made when there is rapid reduction in kidney function, as measured by serum creatinine, or based on a rapid reduction in urine output, termed oliguria.

The management of AKI hinges on identification and treatment of the underlying cause. In addition to treatment of the underlying disorder, management of AKI routinely includes the avoidance of substances that are toxic to the kidneys, called nephrotoxins. These include nonsteroidal anti-inflammatory drugs (NSAIDs) such as ibuprofen, iodinated contrasts such as those used for CT scans, many antibiotics such as gentamicin, and a range of other substances.

The foregoing and other features of the disclosure will become more apparent from the following detailed description of several embodiments which proceeds with reference to the accompanying figures.

SUMMARY

Applicants report the biological behaviors of DONs in mouse and conclude that DONs can be used for treatment of acute kidney injury (AKI). This is the first study to achieve therapeutic effect with DNA origami nanostructures in murine acute kidney injury model. The disclosed PET imaging results show that DONs mainly localized in the kidneys, with low uptake in the liver and intestine. With the murine model, rectangular Rec-DNA origami nanostructures (Rec-DONs) significantly improved excretory function of kidneys with AKI.

Based upon these findings, disclosed herein are compositions and methods for treating acute kidney injury. In some embodiments, the method comprises administering a sufficient amount of a DNA origami nanostructure to a subject afflicted with AKI to increase an excretory function of said subject. For example, the DNA origami nanostructure comprises a scaffold strand and a plurality of staple strands, wherein the scaffold strand comprises a M13 viral genome having a length of 7249 base pairs and each staple strand of the plurality of staple strands has a length of about 20 to 60 base pairs. In some embodiments, the method further comprises providing sufficient conditions to induce a self-assembly of the scaffold strand and the plurality of staple strands into one of a plurality of forms. In some examples, the DNA origami nanostructure comprises a rectangular DNA origami nanostructure. In some examples, the DNA origami nanostructure comprises a triangular DNA origami nanostructure. In some examples, the DNA origami nanostructure comprises a tubular DNA origami nanostructure. In additional embodiments, the method further comprises determining whether the excretory function of the subject is increased by measuring a plurality of end products of nitrogen metabolism in a blood sample of the subject. In some examples, the plurality of end products comprises urea and creatinine. In some embodiments, the disclosed method further comprises reducing an amount of damaged tubulars and glomerulus structures in a kidney of the subject. It is contemplated that the disclosed compositions can be administered by any method sufficient to deliver an effective amount of the nanostructure, including intravenous injection. It is also contemplated that the disclosed nanostructures may be labeled, such as with a radiolabel, including copper-64 ($^{64}Cu$).

BRIEF DESCRIPTION OF THE DRAWINGS

FIG. 3D (right panel) shows partially-folded DONS;
FIG. 9 is hematoxylin and eosin staining of obstructed (asterisks) and damaged (arrows) kidney tubular structures in a mouse model.

DETAILED DESCRIPTION OF SEVERAL EMBODIMENTS

Figure 1B:
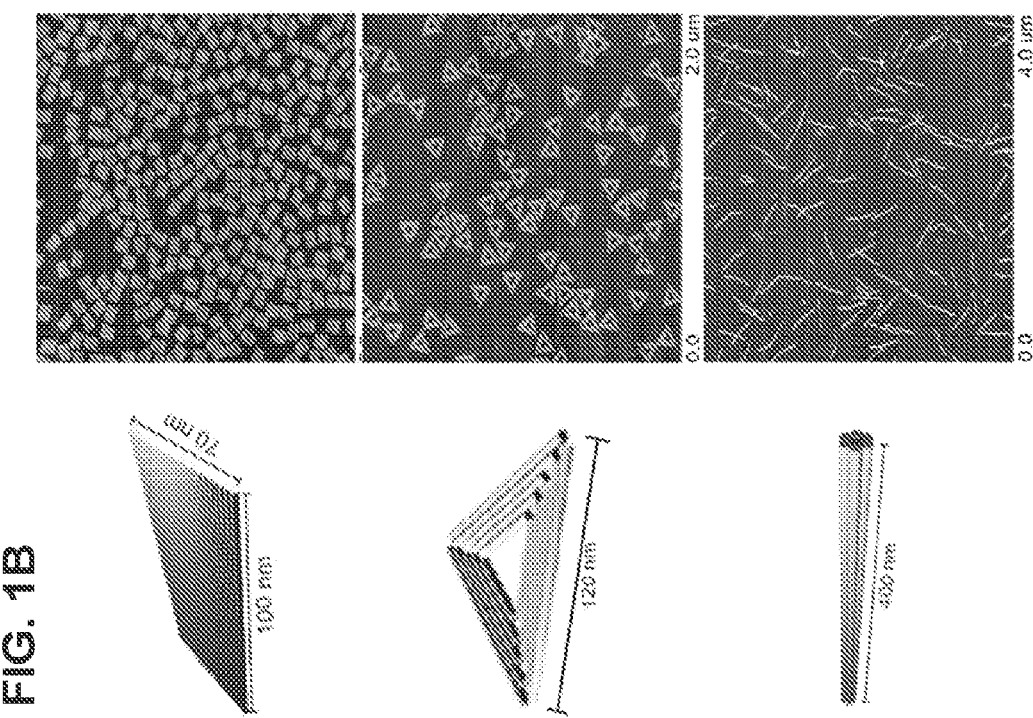
FIG. 1B shows different embodiments of a DON form.

This technology disclosed herein is described in one or more exemplary embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular forms "a," "an," and "the" are intended to include the plural forms as well, unless the context clearly indicates otherwise.

As used herein, the term "and/or" refers to and encompasses any and all possible combinations of one or more of the associated listed items, as well as the lack of combinations when interpreted in the alternative ("or").

As used herein, "one or more" or at least one can mean one, two, three, four, five, six, seven, eight, nine, ten or more, up to any number.

As used herein, the term "comprises" means "includes." Hence "comprising A or B" means including A, B, or A and B. It is further to be understood that all base sizes and all molecular weight or molecular mass values given for nucleic acids are approximate and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. Unless otherwise defined, all technical terms used herein have the same meaning as commonly understood by one of ordinary skill in the art to which this disclosure belongs.

As used herein, the term "administration" or "administering" or "administered" means to provide or give a subject a composition by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes. Parental administered is administration outside of the intestine, for example, not via the alimentary tract. Generally, parenteral formulations are those that will be administered through any possible mode except ingestion. This term especially refers to injections, whether administered intravenously, intrathecally, intramuscularly, intraperitoneally, or subcutaneously. Disclosed compositions may be administered alone and/or simultaneously with one or more other compounds. In some embodiments, the compounds may be administered sequentially, in any order. It will be appreciated that the actual method and order of administration will vary according to, inter alia, the particular preparation of compound (s) being utilized, and the particular formulation (s) of the one or more other compounds being utilized. The optimal method and order of administration of the disclosed compositions for a given set of conditions can be ascertained by those skilled in the art using conventional techniques and in view of the information set out herein. In accordance with good clinical practice, the instant compositions can be administered at a dose that will produce effective beneficial effects without causing undue harmful or untoward side effects, i.e., the benefits associated with administration outweigh the detrimental effects.

As used herein, the term "ameliorate" refers to the ability to make better, or more tolerable, a condition such as an acute kidney injury.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, The Science and Practice of Pharmacy (latest edition)).

As used herein, the term "label" is a detectable substance that is conjugated directly or indirectly to another molecule to facilitate detection of that molecule. Specific, non-limiting examples of labels include fluorescent tags, enzymatic linkages, and radioactive isotopes.

As used herein, the term "nucleic acid" means and includes a polymeric form of nucleotides (e.g., polynucleotides and oligonucleotides) of any length that comprises purine and pyrimidine bases, or chemically or biochemically modified purine and pyrimidine bases. Nucleic acids may comprise single stranded sequences, double stranded sequences, or portions of both double stranded or single stranded sequences. As non-limiting examples, the nucleic acid may include ribonucleic acid (RNA), deoxyribonucleic acid (DNA), peptide nucleic acid (PNA), or combinations thereof. The backbone of the polynucleotide may comprise sugars and phosphate groups as may typically be found in RNA or DNA, or modified sugar and/or phosphate groups. Furthermore, the polynucleotide may comprise modified nucleotides, such as methylated nucleotides and nucleotide analogs. Thus, the terms nucleoside, nucleotide, deoxynucleoside and deoxynucleotide generally include analogs such as those described herein.

Typically, a nucleic acid will comprise phosphodiester bonds, however, nucleic acids may comprise a modified backbone comprising, for example, phosphoramide, phosphorothioate, phosphorodithioate, O-methylphosphoroamidite linkages, and peptide nucleic acid backbones and linkages. Other analog nucleic acids include those with positive backbones; non-ionic backbones and non-ribose backbones. Nucleic acids containing one or more carbocyclic sugars are also included within the definition of nucleic acids. These modifications of the ribose-phosphate backbone may be done to facilitate the addition of electron transfer moieties, or to increase the stability and half-life of such molecules in solution. As will be appreciated by those in the art, all of these nucleic acid analogs may find use in the present disclosure as helper strands or as part of a polynucleotide used to generate the nanostructure. In addition, mixtures of naturally occurring nucleic acids and analogs can be made.

Peptide nucleic acids (PNA) which includes peptide nucleic acid analogs can be used in the methods and compositions of the invention. Such peptide nucleic acids have increased stability. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched basepairs. DNA and RNA typically exhibit a 2-4 degree C. drop in $T_m$ for an internal mismatch. With the non-ionic PNA backbone, the drop is closer to 7-9 degree C. Similarly, due to their non-ionic nature, hybridization of the bases attached to these backbones is relatively insensitive to salt concentration.

As used herein, the terms "prevent," preventing" or "prevention" refer to any type of action that results in the absence, avoidance and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the disclosure.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, rodents (e.g., mice, rats, etc.) and the like. Preferably, the subject is a human patient. In particular embodiments, the subject of this disclosure is a human subject. A "subject in need thereof" or "a subject in need of" is a subject known to have, or is suspected of having acute kidney injury or is at risk of developing acute kidney injury as described herein.

As used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

Compositions

Disclosed embodiments relate generally to nanostructures comprising directed self-assemblies of nucleic acid structures. In some embodiments, the nucleic acid structure may be DNA structure. Non-limiting examples of such DNA structure may include those described in Wei et al. (Complex Shapes Self-Assembled From Single Stranded DNA Tiles, Nature, vol. 485, (2012), 623-627), or the DNA origami structure disclosed in U.S. Pat. No. 8,501,923 each of which is hereby incorporated by reference in its entirety. As used herein, the term "directed self-assembly of multiple DNA structures" or "DSA of multiple DNA structures" refers to a self-assembly of multiple DNA structures.

In some embodiments, a nanostructure comprising a polynucleotide may comprise one or more distinct polymeric nucleic acid structures (e.g., at least 20, at least 50, at least 100, or at least 1000 or more distinct nucleic acid molecules). The nucleic acids may be single stranded or double stranded, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, and the like. Such nucleic acids comprise nucleotides and nucleoside and nucleotide analogs, and modified nucleosides such as amino modified nucleosides. In addition, "nucleoside" includes non-naturally occurring analog.

DNA origami is the nanoscale folding of DNA to create arbitrary two and three-dimensional shapes at the nanoscale. The specificity of the interactions between complementary base pairs make DNA a useful construction material, through design of its base sequences. In some embodiments, the DNA structures may be those DNA structures that are composed of DNA subunits having dimensions of less than 10 nm. In some embodiments, the DNA structures may comprise the DNA origami that has dimensions of 50-200 nm, such as 50, 55, 60, 70, 75, 80, 85, 90, 95, 100, 105, 110, 115, 120, 125, 130, 135, 140, 150, 155, 160, 165, 170, 175, 180, 185, 190, 195, or 200 nm. In some embodiments, a Rec-DON is between 60 nm×120 nm, 60 nm×115 nm, 60 nm×110 nm, 60 nm×105, 60 nm×100 nm, 60×95 nm, 60×90 nm, 65 nm×90 nm, 65 nm×95 nm, 65 nm×100 nm, 65 nm×105 nm, 65 nm×110 nm, 65 nm×115 nm, 65 nm×120, 70 nm×90 nm, 70 nm×95 nm, 70 nm×100 nm, 70 nm×105 nm, 70 nm×110 nm, 70 nm×115 nm, 70 nm×120 nm, 75 nm×90 nm, 75 nm×95 nm, 75×100 nm, 75 nm×105 nm, 75 nm×110 nm, 75 nm×115 nm, or 75 nm×120 nm. In some embodiments, each edge of a Tri-DON is at least 100 nm, such as 100, 105, 110, 115, 120, 125, 130, 135, 140, 145, or 150 nm. In some embodiments, the length of a Tub-DON is between 100 and 500 nm, such as between 200 nm and 400 nm, including 100, 150, 200, 250, 300, 350, 400, 450 or 500 nm.

Methods of Making

Design of scaffolded nucleic acid origami generally comprises building a geometric model of a nucleic acid structure that will approximate the desired shape/geometry. The shape is filled from top to bottom by an even number of parallel double helices, idealized as cylinders. The helices are cut to fit the shape in sequential pairs and are constrained to be an integer number of turns in length. To hold the helices together, a periodic array of crossovers is incorporated; these crossovers designate positions at which strands running along one helix switch to an adjacent helix and continue there. The resulting model approximates the shape within one turn (such as 3.6 nm) in the x-direction and roughly two helical widths (such as 4 nm) in the y-direction. DNA lattice parallel helices in such structures are not close-packed, perhaps owing to electrostatic repulsion. Thus, the exact y-resolution depends on the gap between helices. The gap, in turn, appears to depend on the spacing of crossovers.

The basic technique for creating shapes involves folding a long single stranded polynucleotide, referred to herein as a "scaffold strand", into a desired shape or structure using a number of small "helper strands" as glue to hold the scaffold in place. The number of helper strands will depend upon the size of the scaffold strand and the complexity of the shape or structure. For example, for relatively short scaffold strands (e.g., about 150 to 1500 base in length) and/or simple structures, the number of helper strands may be small (e.g., about 4 to 40, such as 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40). For longer scaffold strands (e.g., greater than 1500 bases) and/or more complex structures, the number of helper strands may be several hundred to thousands. In some examples, the number of helper strands are about 300 to 600, including 300, 400, 500 or 600. In some examples, each staple/helper strand has a length of about 20 to 60 base pairs, such as 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 base pairs.

In some embodiments, the disclosed methods use the short "staple" strands or "helper strands" of nucleic acids to fix a polynucleotide strand into a particular pattern. The choice of staple strands determines the pattern. In one aspect, a software program is used to identify the staple strands needed to form a given design. In some examples, the DNA origami nanostructure comprises a scaffold strand and a plurality of staple/helper strands, wherein the scaffold strand comprises a M13 viral genome having a length of 7249 base pairs; and each staple strand of the plurality of staple/helper strands has a length of about 20 to 60 base pairs.

The disclosure provides methods for creating any desired shape or structure out of a polynucleotide. Once the shape or structure has been created, any desired pattern or ligand may be added to the shape or structure. For example, a triangular structure can be created, and then the numbers 1, 2, and 3 can be added to the arms to differentiate them. In another aspect, a rectangle can be made, and a map of the western hemisphere can be added to the rectangular structure. In some examples, the resolution of the shapes or structures is about 6 nanometers in one direction and about 3 nanometers in the other. For example, with internal labels on helper/staple strands the resolution can be reduced to about 3 nm. This means that, given a desired geometric structure, a polynucleotide structure can be made that matches the contours to within better than 6 nanometers. It is contemplated that this disclosure covers additional shapes or geometries recognized as suitable by those of ordinary skill after studying the present disclosure. After the desired structure has been generated, additional patterns, materials or structures can be added, such as with approximately 6 nanometer resolution.

Several factors contribute to the success of scaffold nucleic acid origami of the disclosure. These include, but are not limited to (1) strand invasion, (2) an excess of staples, (3) cooperative effects and (4) design that intentionally does not rely on binding between staples. Briefly, strand invasion allows correct binding of excess full-length staples to displace unwanted secondary structure, incorrect staples, or grossly truncated staples. Further, each correct addition of a staple organizes the scaffold for subsequent binding of adjacent staples and precludes a large set of undesired secondary structures. Last, because staples are not designed to bind one another, their relative concentrations do not matter.

It will also be recognized the molecular biology techniques can be used to generate a scaffold nucleic acid origami in vivo. Another aspect of the invention pertains to vectors, e.g., expression vectors, containing a nucleic acid encoding at least one (typically a plurality of distinct) helper/staple strands (or a portion thereof). Such helper/staple strands can be expressed in a host organism (e.g., cell) wherein the helper/staple strands interact with a separate endogenous scaffold strand or a separate heterologous scaffold strand (e.g., a scaffold strand present in a separate vector). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the disclosure comprise oligonucleotide helper/staple strands and may include a polynucleotide scaffold strand such that a scaffolded nucleic acid origami is generated upon expression of the vector within the organism or cell. Typically the vector is in a form suitable for expression in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of desired, and the like.

The recombinant expression vectors of the disclosure can be designed for expression of at least one (typically a plurality of distinct) helper/staple strands in prokaryotic or eukaryotic cells, e.g., bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Another aspect of the invention pertains to living organisms (e.g., host cells) into which a recombinant expression vector of the invention or isolated nucleic acid molecule of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, At least one (typically a plurality of distinct) helper/staple strands protein can be expressed in bacterial cells such as E. coli, insect cells, yeast or mammalian cells (such as Chinese hamster ovary cells (CHO) or COS cells). Other suitable host cells are known to those skilled in the art.

Vector DNA or an isolated nucleic acid molecule of the invention can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. and other laboratory manuals.

For stable transfection of mammalian cells, it is known that, depending upon the expression vector and transfection technique used, only a small fraction of cells may integrate the foreign DNA into their genome. In some cases vector DNA is retained by the host cell. In other cases the host cell does not retain vector DNA and retains only an isolated nucleic acid molecule of the invention carried by the vector. In some cases, an isolated nucleic acid molecule of the invention is used to transform a cell without the use of a vector.

In order to identify and select these integrants, a gene that encodes a selectable marker (e.g., resistance to antibiotics) is generally introduced into the host cells along with the nucleic acid of interest. Typical selectable markers include those which confer resistance to drugs, such as G418, hygromycin and methotrexate. Nucleic acid encoding a selectable marker can be introduced into a host cell on the same vector as that encoding at least one (typically a plurality of distinct) helper/staple strands or can be introduced on a separate vector. Cells stably transfected with the introduced nucleic acid can be identified by drug selection (e.g., cells that have incorporated the selectable marker gene will survive, while the other cells die).

Pharmaceutical compositions may be prepared as medicaments to be administered in any method suitable for the subject's condition, for example, orally, parenterally (including subcutaneous, intramuscular, and intravenous), rectally, transdermally, buccally, or nasally. In some examples, a composition is administered with a vehicle, such as a pharmaceutically acceptable vehicle.

A pharmaceutically acceptable vehicle is a material that is not biologically or otherwise undesirable, i.e., the material may be administered to a subject along with a disclosed composition, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., Remington's Pharmaceutical Science; latest edition). Exemplary pharmaceutically acceptable carriers for compositions disclosed herein include, but are not limited to, sterile pyrogen-free water and sterile pyrogen-free physiological saline solution, as well as other carriers suitable for injection into and/or delivery to a subject, particularly a human subject, as would be well known in the art.

Suitable forms for oral administration include, but are not limited to, tablets, powders, compressed or coated pills, dragees, sachets, hard or gelatin capsules, sub-lingual tablets, syrups, and suspensions. Suitable forms of parenteral administration include, but are not limited to, an aqueous or non-aqueous solution or emulsion. Suitable forms for rectal administration, include, but are not limited to, suppositories with hydrophilic or hydrophobic vehicles. For topical administration, suitable forms include, but are not limited to, suitable transdermal delivery systems known in the art, such as patches, and for nasal delivery, suitable forms include, but are not limited to, aerosol and nebulized delivery systems known in the art.

In addition to the nanostructures provided herein, a composition of the present disclosure (e.g., a pharmaceutical composition) may contain one or more excipients or adjuvants. Selection of excipients and/or adjuvants and the amounts to use may be readily determined by the formulation scientist upon experience and consideration of standard procedures and reference works in the field.

Excipients such as diluents increase the bulk of a solid pharmaceutical composition, and may make a pharmaceutical dosage form containing the composition easier for the patient and caregiver to handle. Diluents for solid compositions include, but are not limited to, microcrystalline cellulose, microfme cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates, potassium chloride, powdered cellulose, sodium chloride, sorbitol, or talc.

Solid pharmaceutical compositions that are compacted into a dosage form, such as a tablet, may include, but are not limited to, excipients whose functions include, but are not limited to, helping to bind the active ingredient and other excipients together after compression, such as binders. Binders for solid pharmaceutical compositions include, but are not limited to, acacia, alginic acid, carbomer, carboxymethylcellulose sodium, dextrin, ethyl cellulose, gelatin, guar gum, hydrogenated vegetable oil, hydroxyethyl cellulose, hydroxypropyl cellulose, hydroxypropyl methyl cellulose, liquid glucose, magnesium aluminum silicate, maltodextrin, methylcellulose, polymethacrylates, povidone, pregelatinized starch, sodium alginate, or starch.

The dissolution rate of a compacted solid pharmaceutical composition in the patient's stomach may be increased by the addition of a disintegrant to the composition. Excipients which function as disintegrants include, but are not limited to, alginic acid, carboxymethylcellulose calcium, carboxymethylcellulose sodium, colloidal silicon dioxide, croscarmellose sodium, crospovidone, guar gum, magnesium aluminum silicate, methyl cellulose, microcrystalline cellulose, polacrilin potassium, powdered cellulose, pregelatinized starch, sodium alginate, sodium starch glycolate, or starch.

Glidants can be added to improve the flowability of a non-compacted solid composition and to improve the accuracy of dosing. Excipients that may function as glidants include, but are not limited to, colloidal silicon dioxide, magnesium trisilicate, powdered cellulose, starch, talc, or tribasic calcium phosphate.

When a dosage form such as a tablet is made by the compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease the release of the product from the die. Excipients that function as lubricants include, but are not limited to, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, or zinc stearate.

Flavoring agents and flavor enhancers make the dosage form more palatable to the patient. Common flavoring agents and flavor enhancers for pharmaceutical products that may be included in the composition of the invention include, but are not limited to, maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present disclosure, the active ingredient and any other solid excipients are suspended in a liquid carrier such as water, vegetable oil, alcohol, polyethylene glycol, propylene glycol, or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the invention include, but are not limited to, gelatin, egg yolk, casein, cholesterol, acacia, tragacanth, chondrus, pectin, methyl cellulose, carbomer, cetostearyl alcohol, or cetyl alcohol.

Liquid pharmaceutical compositions of the present disclosure may also contain a viscosity enhancing agent to improve the mouth-feel of the product and/or coat the lining of the gastrointestinal tract. Such agents include, but are not limited to, acacia, alginic acid, bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, or xanthan gum.

Sweetening agents such as sorbitol, saccharin, sodium saccharin, sucrose, aspartame, fructose, mannitol, or invert sugar may be added to improve the taste. Preservatives and chelating agents such as alcohol, sodium benzoate, butylated hydroxy toluene, butylated hydroxyanisole, or ethylenediamine tetraacetic acid may be added at levels safe for ingestion to improve storage stability.

According to the disclosure, a liquid composition may also contain a buffer such as gluconic acid, lactic acid, citric acid or acetic acid, sodium gluconate, sodium lactate, sodium citrate, or sodium acetate.

Methods of Use

Methods of treating an acute kidney injury in a subject are provided. In some examples, the method includes administering to a subject in need thereof an effective amount of a disclosed composition, such as a disclosed pharmaceutical composition to inhibit, reduce, ameliorate and/or prevent acute kidney injury. In some examples, a disclosed composition may be administered alone, simultaneously with one or more other compounds, or the compounds may be administered sequentially, in either order. It will be appreciated that the actual method and order of administration will vary according to, the particular preparation of compound(s) being utilized, the particular formulation(s) of the one or more other compounds being utilized, and the conditions to be treated. The optimal method and order of administration of the compounds of the disclosure for a given set of conditions can be ascertained by those skilled in the art using conventional techniques and in view of the information set out herein. In accordance with good clinical practice, it is preferred to administer the instant compounds at a concentration level which will produce effective beneficial effects without causing significant or substantial harmful or untoward side effects. In prophylactic applications, pharmaceutical compositions or medicaments are administered to a subject susceptible to, or otherwise at risk of, suffering acute kidney injury in an amount sufficient to eliminate or reduce the risk, lessen the severity, or delay the outset of the injury, including biochemical, histologic and/or physiologic symptoms of the injury. In therapeutic applications, compositions or medicants are administered to a subject suspected of, or already suffering from such an injury in an amount sufficient to treat, or at least partially reduce or arrest, the symptoms of the injury (biochemical, histologic and/or physiological). An amount adequate to accomplish therapeutic or prophylactic treatment is defined as an effective amount or a therapeutically or prophylactically effective dose. In either prophylactic or therapeutic regimens, disclosed compositions can be and are usually administered in several doses until a desired effect has been achieved.

An effective dose or effective doses of the disclosed compositions can vary depending upon many different factors, including means of administration, target site, physiological state of the subject, whether the subject is human or an animal, other medications administered, and/or whether treatment is prophylactic or therapeutic. In some embodiments, the subject is a human but nonhuman mammals including transgenic mammals can also be treated. Treatment dosages can be titrated to optimize safety and efficacy. Generally, an effective amount of the nanostructures and compositions disclosed herein will be determined by the age, weight and condition or severity of disease or disorder of the subject.

The amount of nanostructure can depend on whether additional compounds, such as pharmaceutical carriers, are also administered, with higher dosages being required in the absence of additional compounds. The amount of a nanostructure for administration according to the disclosed methods can be from about 1 µg to about 50 mg. For example, a subject can be administered about 1 µg to about 500 µg per administration or about 10 mg to 20 mg per subject per administration and more usually from about 20 mg to 35 mg per administration for human administration. In some embodiments, a higher dose of 50 mg per administration can be used. Typically, about 10, 20, 35, or 50 mg is used for each human administration.

Generally, dosing (e.g., an administration) can be one or more times daily, or less frequently, such as once a day, once a week, once a month, once a year, to once in a decade, etc. and may be in conjunction with other compositions as described herein. In certain embodiments, the dosage is greater than about 1 µg/subject and usually greater than about 10 µg/subject if additional compounds are also administered, and greater than about 100 µg/subject in the absence of additional compounds, such as a pharmaceutical carrier. In other examples, such as in a human subject, the dosage is greater than 10 mg/subject and usually greater than about 20 mg/subject if additional compounds are also administered, and greater than about 35 mg/subject in the absence of additional compounds, such as a pharmaceutical carrier.

An example of a possible dosage regimen may comprise or consist of an initial administration of a disclosed composition at initial identification of the injury, followed by booster injections at selected time intervals, such as 1 hour, 2 hour, 12 hour, 1 day or 1 week intervals. The dosage and frequency of administration can vary depending on whether the treatment is prophylactic or therapeutic. In prophylactic applications, a relatively low dosage can be administered at relatively infrequent intervals over a long period of time. Some patients may continue to receive treatment for the rest of their lives. In therapeutic applications, a relatively high dosage at relatively short intervals is sometimes appropriate until severity of the injury is reduced or terminated, and typically until the subject shows partial or complete amelioration of symptoms of injury. Thereafter, the subject can be administered a prophylactic regimen.

The aforementioned embodiments are not exclusive and may be combined in whole or in part in any combination.

As will be understood by one skilled in the art, there are several embodiments and elements for each aspect of the invention, and all combinations of different elements are hereby contemplated so the specific combinations exemplified herein are not to be construed as limitations in the scope of the invention as claimed. If specific elements are removed or added to the group of elements available in a combination, then the group of elements is to be construed as having incorporated such a change.

The various techniques, methods, and aspects of the invention described herein can be implemented in part or in whole using computer-based systems and methods. Additionally, computer-based systems and methods can be used to augment or enhance the functionality described herein, increase the speed at which the methods can be performed, and provide additional features and aspects as a part of or in addition to those of the invention described elsewhere in this document. Various computer-based systems, methods and implementations in accordance with the above-described technology are presented below.

A processor-based system can include a main memory, such as random access memory (RAM), and can also include a secondary memory. The secondary memory can include, for example, a hard disk drive and/or a removable storage drive, representing a floppy disk drive, a magnetic tape drive, an optical disk drive, etc. The removable storage drive reads from and/or writes to a removable storage medium. Removable storage medium refers to a floppy disk, magnetic tape, optical disk, and the like, which is read by and written to by a removable storage drive. As will be appreciated, the removable storage medium can comprise computer software and/or data.

In alternative embodiments, the secondary memory may include other similar means for allowing computer programs or other instructions to be loaded into a computer system. Such means can include, for example, a removable storage unit and an interface. Examples of such can include a program cartridge and cartridge interface (such as the found in video game devices), a movable memory chip (such as an EPROM or PROM) and associated socket, and other removable storage units and interfaces, which allow software and data to be transferred from the removable storage unit to the computer system.

The computer system can also include a communications interface. Communications interfaces allow software and data to be transferred between computer system and external devices. Examples of communications interfaces can include a modem, a network interface (such as, for example, an Ethernet card), a communications port, a PCMCIA slot and card, and the like. Software and data transferred via a communications interface are in the form of signals, which can be electronic, electromagnetic, optical or other signals capable of being received by a communications interface. These signals are provided to communications interface via a channel capable of carrying signals and can be implemented using a wireless medium, wire or cable, fiber optics or other communications medium. Some examples of a channel can include a phone line, a cellular phone link, an RF link, a network interface, and other communications channels.

In this document, the terms "computer program medium" and "computer usable medium" are used to refer generally to media such as a removable storage device, a disk capable of installation in a disk drive, and signals on a channel. These computer program products are means for providing software or program instructions to a computer system.

Computer programs (also called computer control logic) are stored in main memory and/or secondary memory. Computer programs can also be received via a communications interface. Such computer programs, when executed, enable the computer system to perform the features of the invention as discussed herein. In particular, the computer programs, when executed, enable the processor to perform the features of the invention. Accordingly, such computer programs represent controllers of the computer system.

In an embodiment where the elements are implemented using software, the software may be stored in, or transmitted via, a computer program product and loaded into a computer system using a removable storage drive, hard drive or communications interface. The control logic (software), when executed by the processor, causes the processor to perform the functions of the invention as described herein.

In another embodiment, the elements are implemented primarily in hardware using, for example, hardware components such as PALs, application specific integrated circuits (ASICs) or other hardware components. Implementation of a hardware state machine so as to perform the functions described herein will be apparent to person skilled in the relevant art(s). In yet another embodiment, elements are implanted using a combination of both hardware and software.

In another embodiment, the computer-based methods can be accessed or implemented over the World Wide Web by providing access via a Web Page to the methods of the invention. Accordingly, the Web Page is identified by a Universal Resource Locator (URL). The URL denotes both the server machine and the particular file or page on that machine. In this embodiment, it is envisioned that a consumer or client computer system interacts with a browser to select a particular URL, which in turn causes the browser to send a request for that URL or page to the server identified in the URL. Typically the server responds to the request by retrieving the requested page and transmitting the data for that page back to the requesting client computer system (the client/server interaction is typically performed in accordance with the hypertext transport protocol ("HTTP")). The selected page is then displayed to the user on the client's display screen. The client may then cause the server containing a computer program of the invention to launch an application to, for example, perform an analysis according to the invention.

Figure 1A:
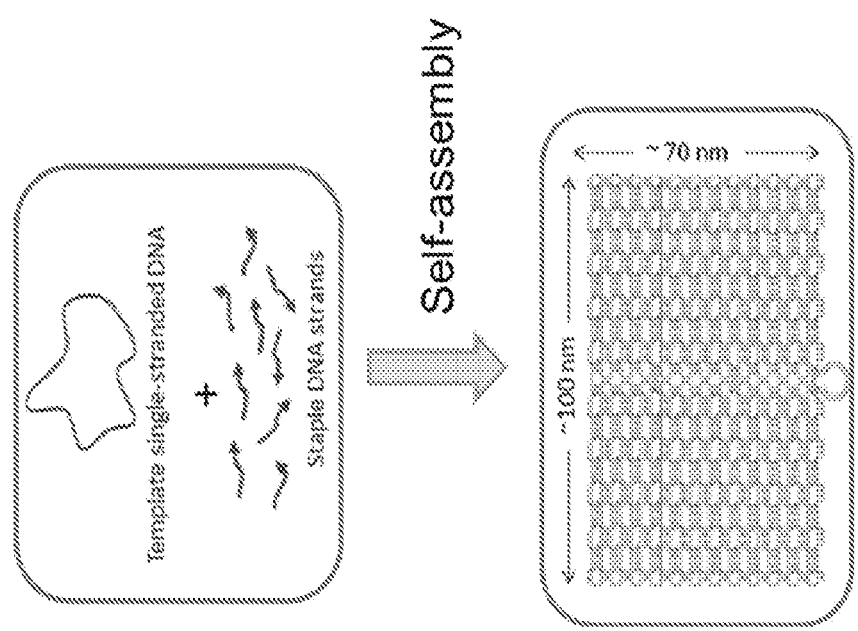
FIG. 1A illustrates an embodiment of forming a DON.

Referring to FIG. 1A, exemplary DNA origami nanostructures are composed of ssDNA (M13 phage) refolded with complementary ssDNA "staple" sequences into computer design-aided predetermined shapes with selected staples extended with complementary sequences to TCR alpha and beta constant region mRNA. Methods for high efficiency transfection of primary T cells with the developed structures, isolation of DNA origami from transfected cells with specifically bound TCR mRNA, as well as a molecular approach for linking the CDR3 from the TCR alpha and beta mRNA into a single cDNA molecule for use in multiplex CDR3 paired end sequencing using existing technologies also are disclosed.

Referring to FIG. 1B, in certain embodiments, three different DONs (rectangular DON, triangular DON and tubular DON) were formed by using different short single strand of DNA (staple strands) and a long single strand DNA. Numerous short staple strands were designed to direct the folding of a long single strand DNA into rectangular, triangular, and/or tubular shapes. For each sample, about 20 nM single-stranded M13mp18 DNA (7,249 nucleotides) was mixed with a 10-fold molar excess of staple strands. The mixture was annealed from about 95° C. to 4° C. with the temperature gradient. The excess staple strands were removed by repeated (3 times) washing and filtered using 100 kD 500 µl Amicon filters. While specific values chosen for this embodiment are recited, it is to be understood that, within the scope of the technology, the values of all of parameters may vary over wide ranges to suit different applications. The atomic force microscopy (AFM) images were shown in FIG. 1B to demonstrate the yield and the purity of DNA origami nanostructures.

Figure 2:
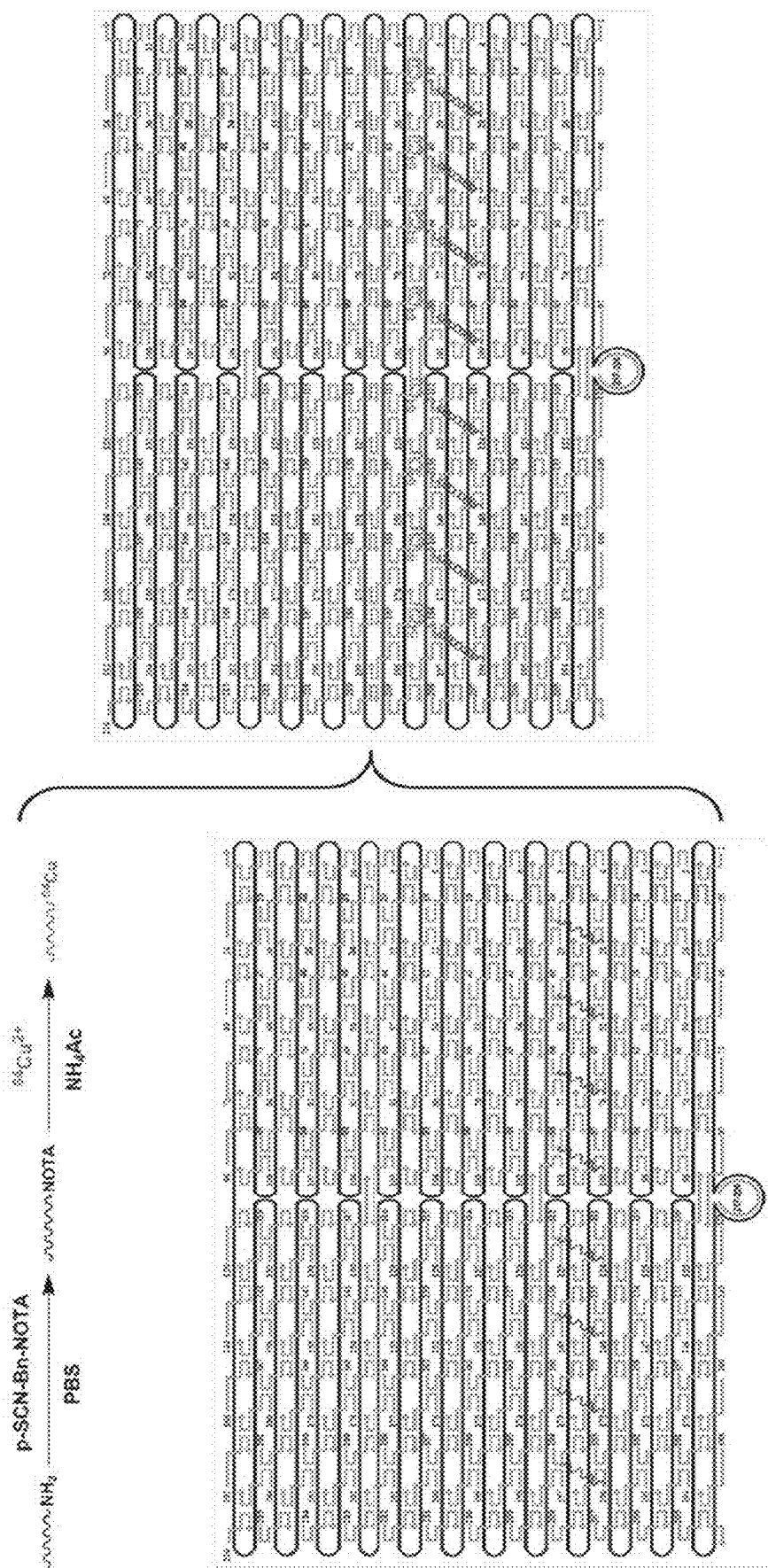
FIG. 2 shows the radiolabeling process of an embodiment of a DON.

Referring to FIG. 2, in certain embodiment, three different DONs (Rectangular DON, Rec-DON; triangular DON, Tri-DON; and tubular DON, Tub-DON) are radiolabeled with Copper-64. Further, positron emission tomography (PET) is used to investigate their pharmacokinetics and biodistribution patterns in vivo.

Figure 4:
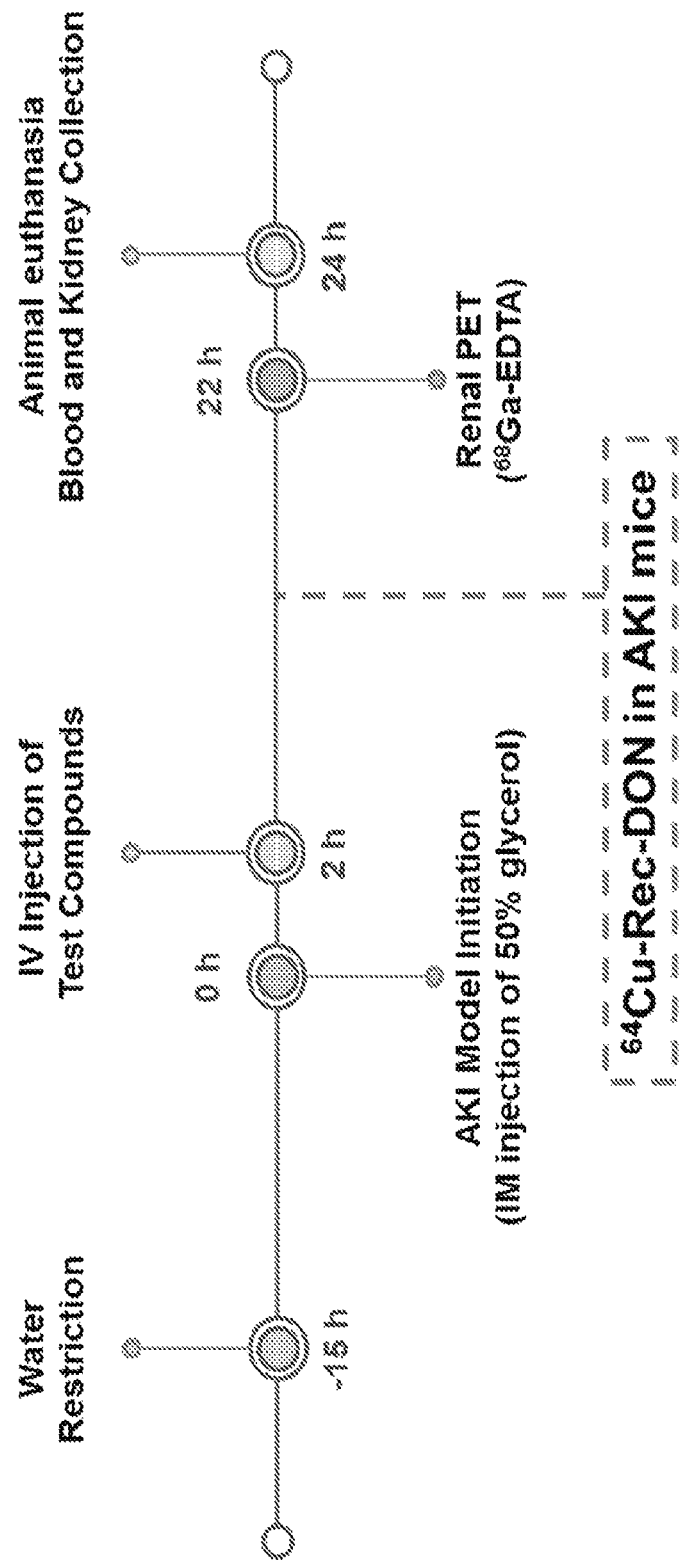
FIG. 4 illustrates an exemplary treatment schedule.

Referring to FIG. 4, AKI is induced in ICR mice with injection of 50% glycerol intramuscularly. And Rec-DONs were administrated as a test drug to protect kidneys 2 hours after AKI induction. Phosphate buffered saline (PBS) and M13 were used as controls. 24 hours after AKI induction, a 30-minute PET imaging with $^{68}$Ga-EDTA (a clinically-used PET tracer for evaluation of renal function) was conducted for all mice (healthy group, Rec-DON-treated group, and PBS-treated group) to non-invasively evaluate kidney functions of all groups, then blood and kidney samples were collected for further validating of the treatment effect.

Figure 3B:
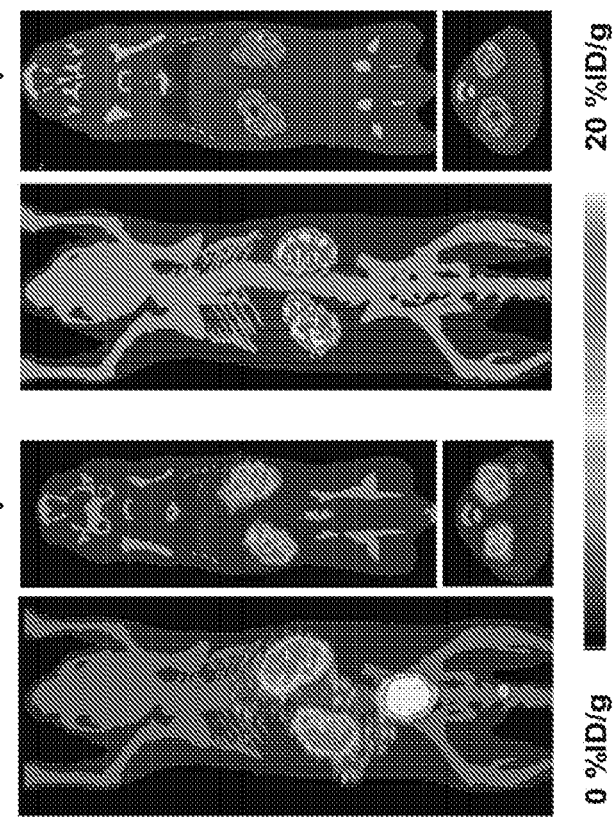
FIG. 3B shows uptake of rectangular DONs in kidneys of normal ICR mice.
Figure 3C:
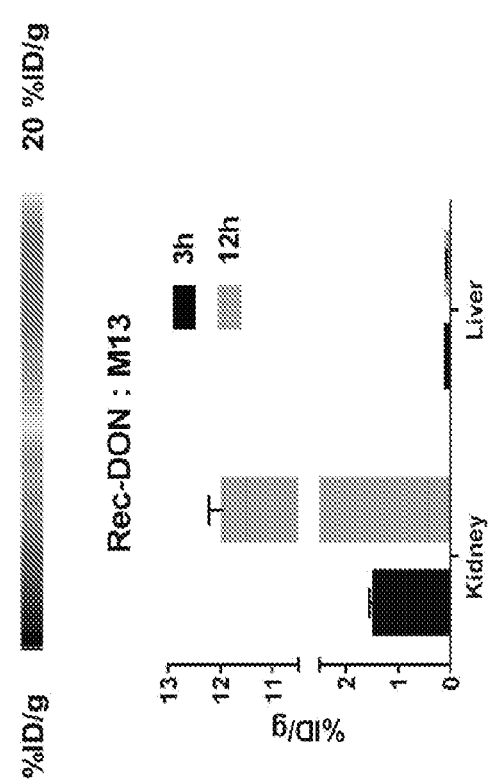
FIG. 3C shows the different bio-distribution pattern of M13 and rectangular DON.
Figure 3A:
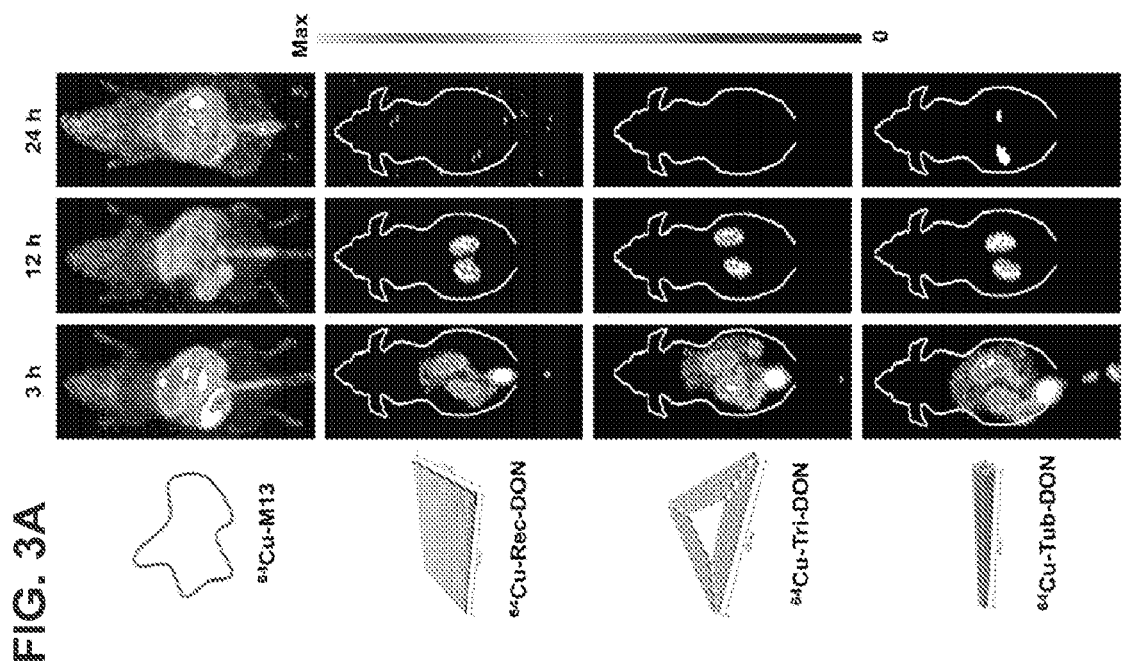
FIG. 3A shows bio-distribution of M13 (unfolded DNA plasmid) and DONs in normal ICR mice.

Referring to FIGS. 3A and 3B, based on the PET imaging of M13 and different DONs in normal ICR mice, only well-folded DONs were prone to accumulate in the kidney, with minor uptake in the liver and intestine as well, whereas M13 showed a high uptake in the liver and GI tract, with minimal uptake in the kidneys. For example, for Rec-DON, a desired size is 70 nm×100 nm; for Tri-DON, each edge is 120 nm, and for Tub-DON, the length is 400 nm. Among all three DONs investigated, Rec-DONs presented the highest kidney uptake.

Figure 3E:
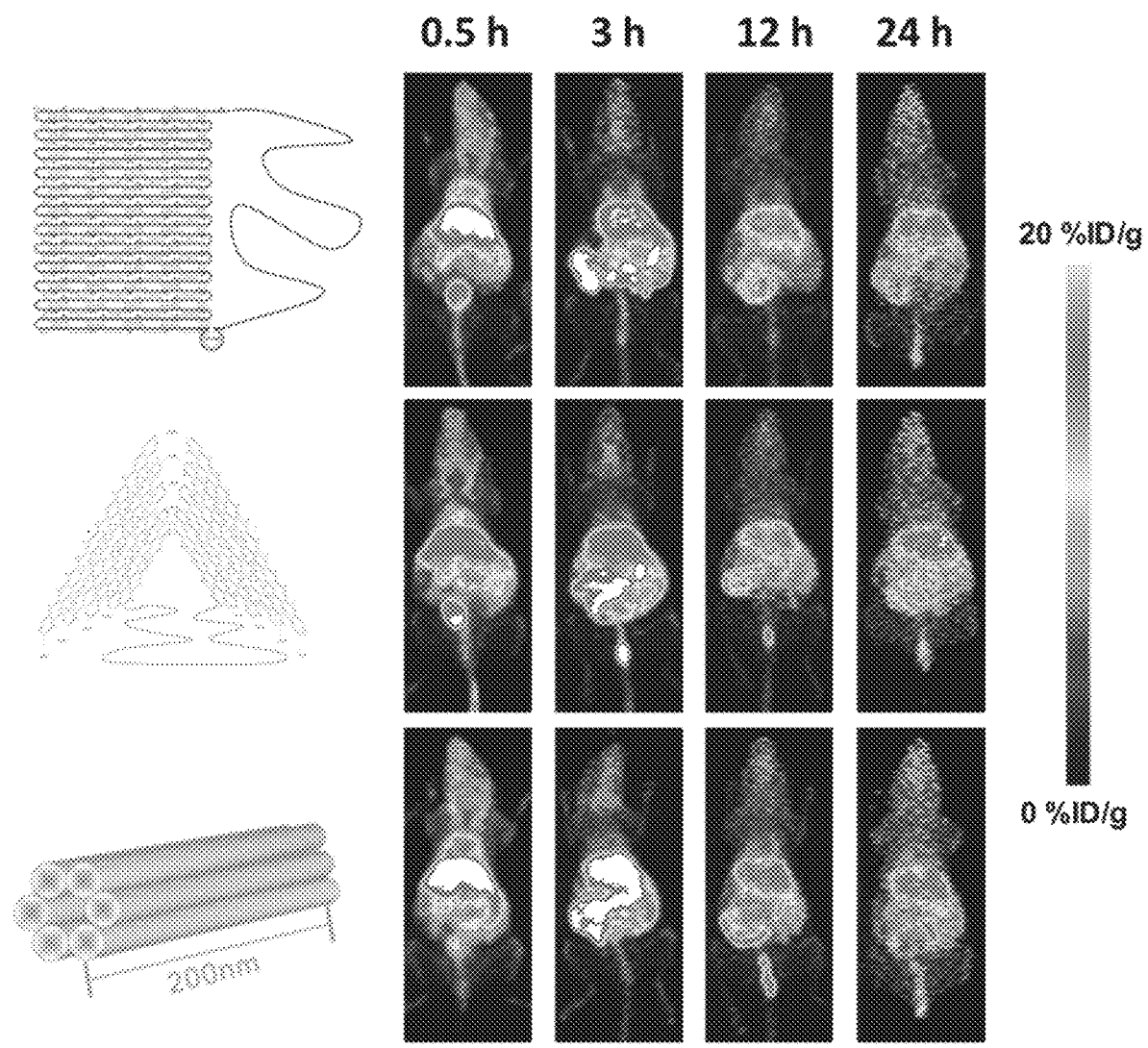
FIG. 3E shows PET imaging results for partially-folded DONS.

FIG. 3D illustrates DONs that were partially folded and the PET images with such DONS are shown in FIG. 3E. As illustrated in FIG. 3D, partially folded DONs were missing significant parts of the designed structures. Use of the term DON standing alone refers to the fully-folded structure unless used in conjunction with partially folded.

Figure 5:
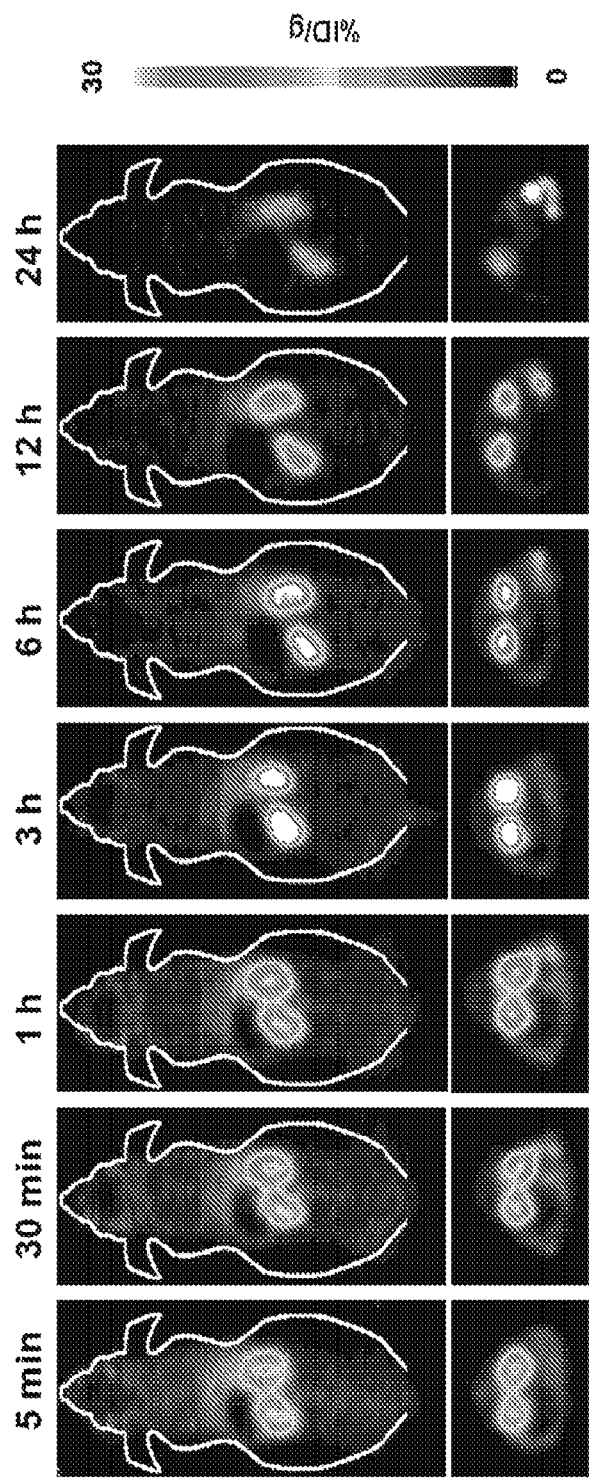
FIG. 5 shows the renal accumulation of rectangular DON in murine models of AKI.

Referring to FIG. 5, $^{64}$Cu-labeled Rec-DON (60 nm×90 nm) showed kidney-targeting properties in AKI mice at different time points after the model initiation. It is contemplated that additional labels can be used depending upon the method of measurement, including fluorophores, photon-emitting molecules and/or other positron emission tomography (PET) isotopes. For example, DONs labeled with fluorophores (such as Cy3, Cy5 and the like) can be used for fluorescent imaging, photon-emitting Tc-99m for SPECT imaging, and other PET isotopes (such as Zr-89) for PET imaging.

Figure 6A:
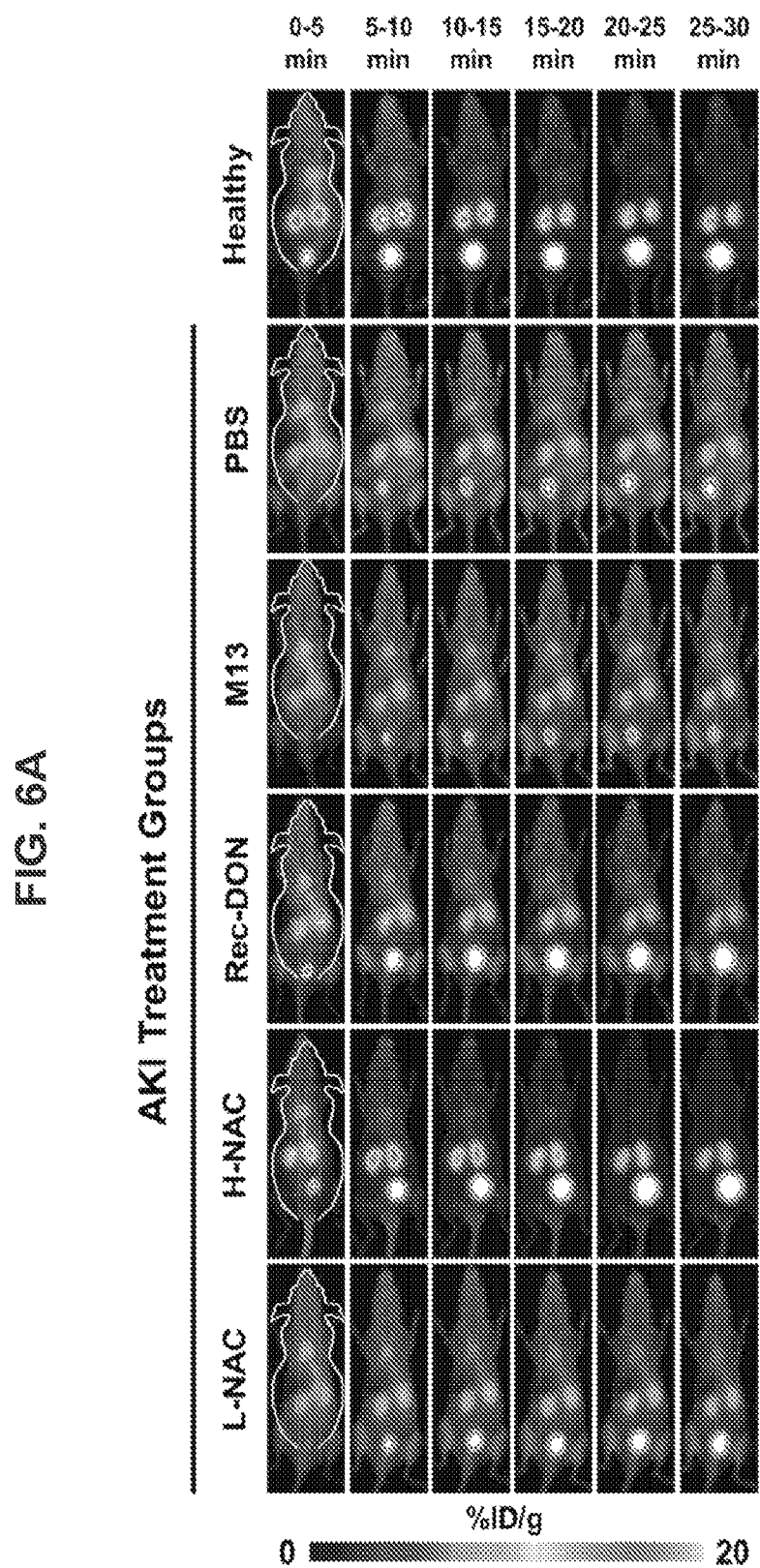
FIG. 6A shows uptake of $^{68}Ga$-EDTA (an imaging agent commonly used for evaluating renal function) in a mouse model compared to controls.
Figures 6B, 6C, 6D:
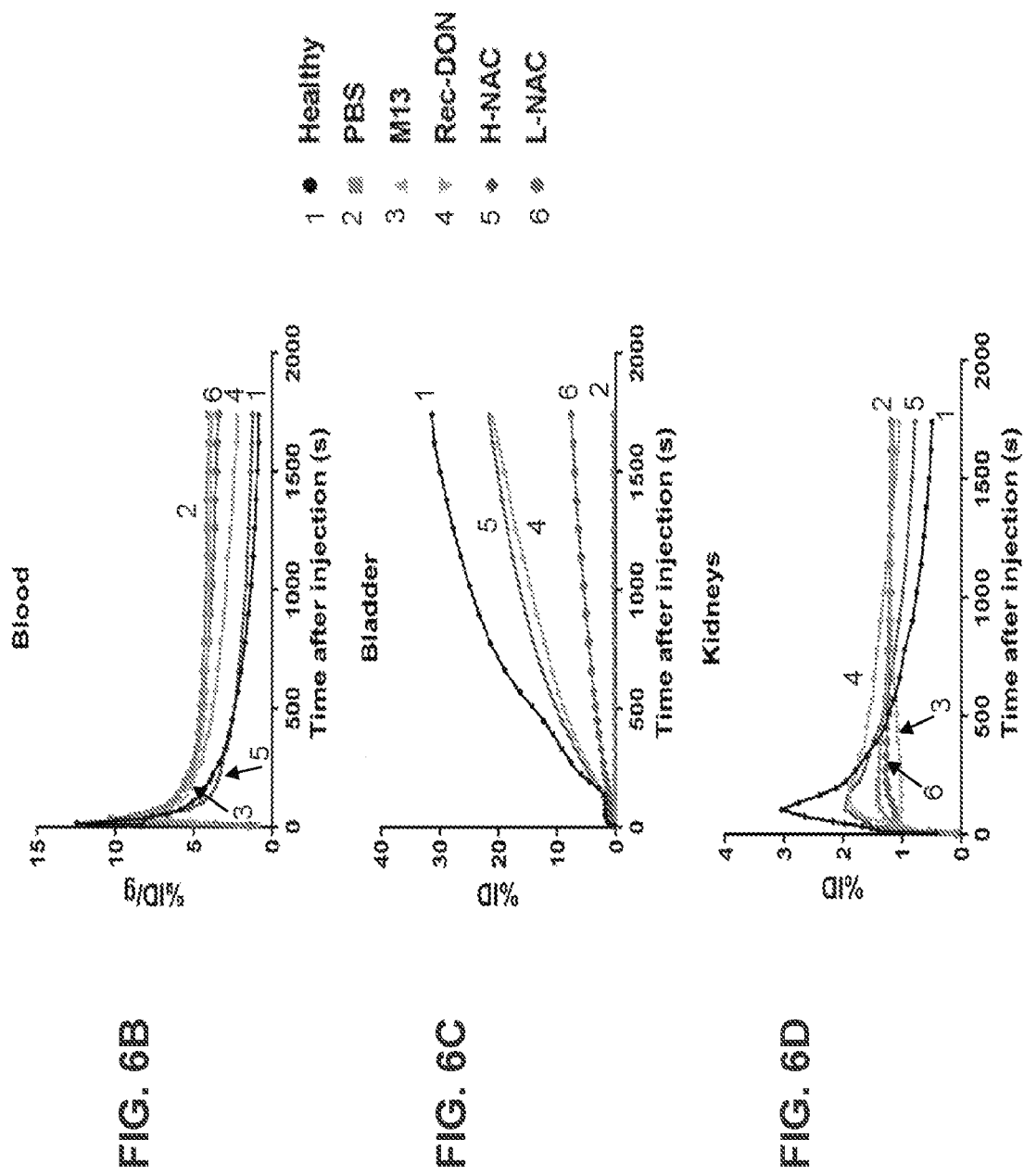
FIGS. 6B-6D show quantitative uptake of $^{68}Ga$-EDTA in a mouse model compared to controls.
Figure 7:
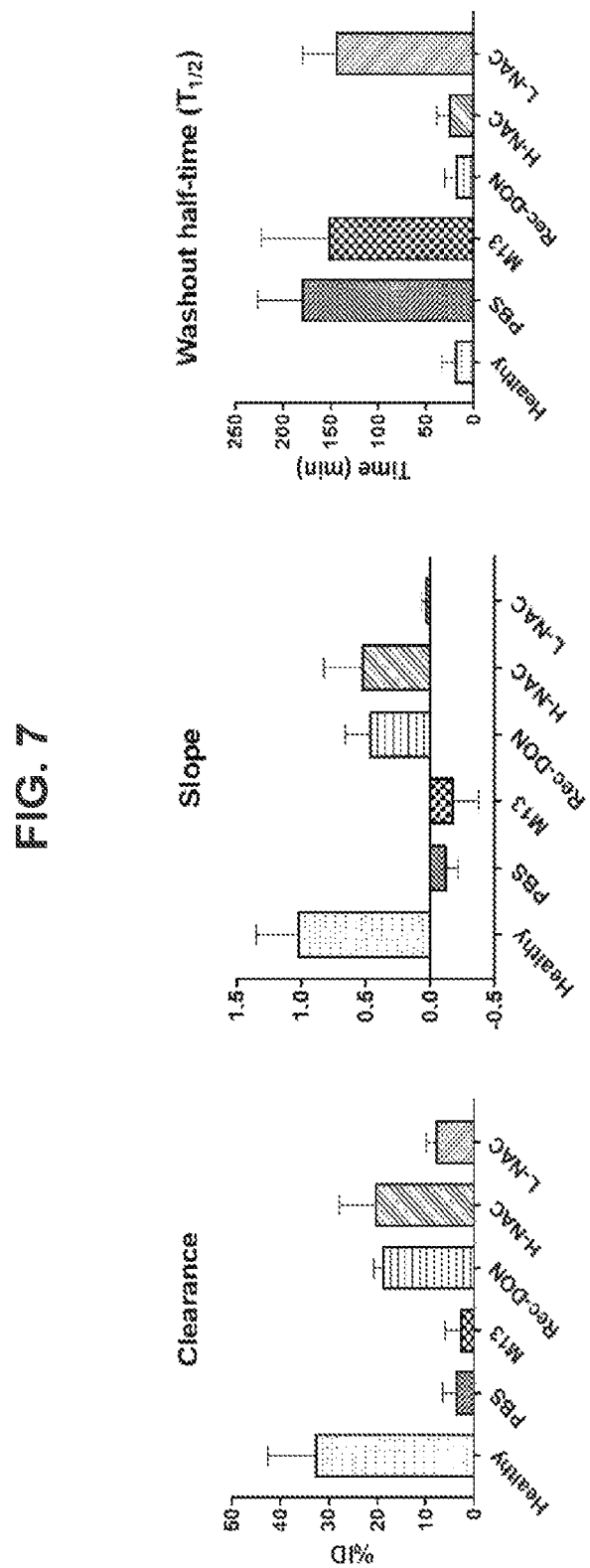
FIG. 7 illustrates the renal function evaluation generated from quantitative data of $^{68}Ga$-EDTA PET imaging.

Monitoring of renal function, by serial serum creatinine measurements and monitoring of urine output, is routinely performed to evaluate the effectiveness of the treatment of AKI. Referring to FIGS. 6 and 7, the excretory function of AKI mice was re-established by administrating Rec-DONs (10 µg/mouse) 2 hours after AKI induction based on the PET imaging with $^{68}$Ga-EDTA, while PBS and M13 could not improve the renal excretion of $^{68}$Ga-EDTA in AKI mice, indicating the active protection of Rec-DONs for the kidneys. The observed high bladder uptake indicates better renal excretory function. Further, Rec-DONs (10 ng/mouse) exhibited similar treatment efficacy as N-acetyl cysteine (NAC, a widely applied antioxidant for contrast-induced AKI) at the higher dose (4.2 mg/mouse). In FIG. 7, clearance is the amount of $^{68}$Ga-EDTA excreted to the bladder. SIU is the sloped of initial uptake, the slope of the kidneys time-activity curve (TAC) from 1-2 minutes. Washout half-time is the half-life of $^{68}$Ga-EDTA in the kidneys measured by applying a one-compartment fitting model.

Figure 8B:
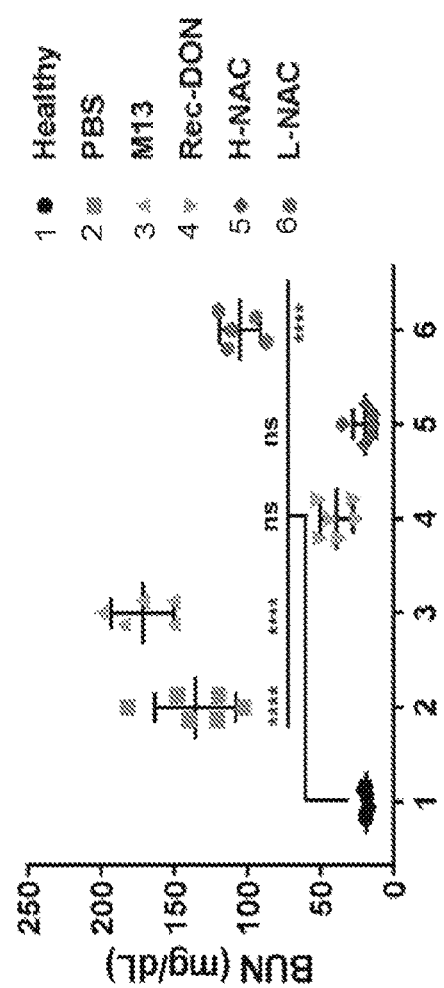
FIGS. 8A-8B shows decreased levels of creatinine and urea nitrogen in blood after DON treatment.
Figure 8A:
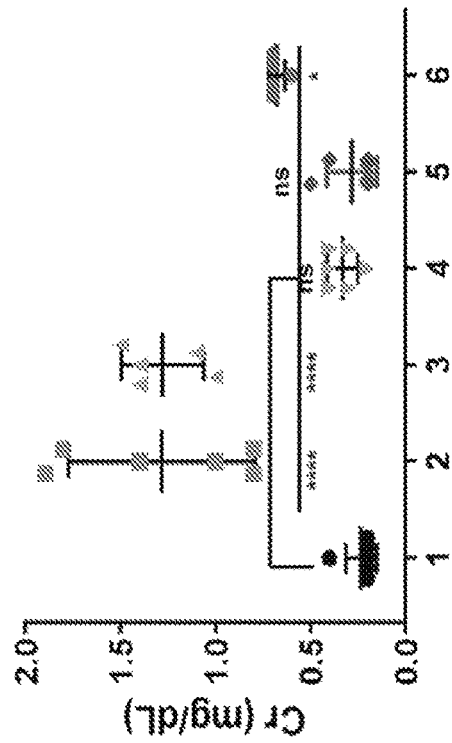

Referring to FIGS. 8A and 8B, blood tests of end products of nitrogen metabolism (urea and creatinine) showed that both PBS group and M13 group had a high level of blood urea nitrogen (BUN) as well as creatinine (Cr), while healthy ICR mice and Rec-DON-treated AKI mice both exhibited low BUN and Cr level. N-acetyl cysteine (NAC) is a clinically-used small molecule for protection of CT contrast agent-induced kidney damage. Different doses (high and low) of NAC (4.2 mg and 0.01 mg per mouse) were also used to display the therapeutic efficacy of DON. DON group exhibited a significantly better treatment effect over NAC group at a lower dose, and a similar therapeutic effect with high-dose NAC group.

Referring to FIG. 9, H&E staining of kidney tissue sections revealed large amount of casts (destroyed kidney tubulars and glomerulus structures) in the PBS group, M13 group, and Low-dose NAC group, while no casts could be found in the healthy group, and few in the Rec-DON- and High-dose NAC-treated group.

The aforementioned studies are the first to achieve therapeutic effects with DNA origami nanostructures in murine acute kidney injury model. The PET imaging results showed that DONs mainly localized in the kidneys, with low uptake in the liver and intestine. With the murine model, Rec-DONs significantly improved excretory function of kidneys with AKI. These studies show that DONs can be used to treat AKI.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims. We therefore claim as our invention all that comes within the scope and spirit of these claims.

We claim:

1. A method of treating acute kidney injury (AKI), the method comprising administering an effective amount of a DNA origami nanostructure to a subject afflicted with AKI to increase an excretory function of said subject.

2. The method of claim 1, wherein the DNA origami nanostructure comprises a scaffold strand and a plurality of staple strands, wherein:
   the scaffold strand comprises a M13 viral genome having a length of 7249 base pairs; and
   each staple strand of the plurality of staple strands has a length of about 20 to 60 base pairs.

3. The method of claim 1, further comprising providing sufficient conditions to induce a self-assembly of the scaffold strand and the plurality of staple strands into one of a plurality of forms.

4. The method of claim 3, wherein the DNA origami nanostructure comprises a rectangular DNA origami nanostructure.

5. The method of claim 3, wherein the DNA origami nanostructure comprises a triangular DNA origami nanostructure.

6. The method of claim 3, wherein the DNA origami nanostructure comprises a tubular DNA origami nanostructure.

7. The method of claim 2, further comprising determining whether the excretory function of the subject is increased by measuring a plurality of end products of nitrogen metabolism in a blood sample of the subject.

8. The method of claim 7, wherein the plurality of end products comprises urea and creatinine.

* * * * *